United States Patent [19]

Kosak

[11] 4,000,252
[45] Dec. 28, 1976

[54] IMMUNOSCINTILLATION CELL

[76] Inventor: Kenneth Kosak, 3194 S. 4400 West, Salt Lake City, Utah 84120

[22] Filed: Jan. 4, 1974

[21] Appl. No.: 430,921

[52] U.S. Cl. .............................. 424/1; 23/230 B; 23/230.3; 23/253 R; 250/303; 250/361 R; 250/362; 250/363 R; 424/1.5; 424/12

[51] Int. Cl.² .................. G01N 33/00; G01T 1/16; A61K 39/00; G01N 33/16

[58] Field of Search .......... 250/303, 304, 361, 362, 250/364; 424/1, 12; 23/230 B, 230.3, 253 R

[56] References Cited

UNITED STATES PATENTS

| | | | |
|---|---|---|---|
| 3,206,602 | 9/1965 | Eberle | 250/364 |
| 3,404,270 | 10/1968 | Ross | 250/364 |
| 3,573,220 | 3/1971 | Benson | 250/362 X |
| 3,758,412 | 9/1973 | Grum et al. | 250/362 |
| 3,798,448 | 3/1974 | Menefee et al. | 250/361 |

OTHER PUBLICATIONS

Ayad, Laboratory Practice, vol. 21, No. 10, Oct. 1972.

*Primary Examiner*—Benjamin R. Padgett
*Assistant Examiner*—Christine M. Nucker
*Attorney, Agent, or Firm*—Richard F. Bojanowski

[57] ABSTRACT

A means and method of radioimmunoassay is disclosed whereby an insolubilized or solid phosphor and binding agent such as an antibody are associated by chemical or physical means to provide a solid scintillating immunoadsorbent cell. This cell is capable of selectively binding or retaining radioactive or labeled antigens and transmitting radioactive energy to a phosphor or photon emitting substance. The luminescence emitted by the phosphor is measured by a scintillator counter and is directly proportional to the radioactive energy released by the labeled antigen bound to the antibody. Upon completion of the measurement the labeled antigens are separated from the antibody and removed from the cell which may now be used for additional analysis. A convenient means for obtaining a solid phosphor and/or binding agent is to combine them by physical or chemical means or to shield one from the other by a separating barrier. In addition the phosphor and/or the binding agent can be attached to an insoluble support medium which can take various structured shapes and forms.

15 Claims, 12 Drawing Figures

IMMUNOSCINTILLATION CELL

BACKGROUND OF THE INVENTION

1. Field

This invention is directed to a means and method of solid phase radioimmunoassay and particularly to a solid scintillating immunoadsorbent cell capable of selectively retaining labeled materials in close proximity to a phosphor.

2. State of the Art

Radioimmunoassay, also referred to as radioimmune assay, competitive radioassay, radiostereoassay or immune radiometric analysis, is a known analytical technique for quantitatively measuring specific proteins, polypeptides and biological agents such as insulin, hormones, enzymes, antigens and the like by the use of radioactive isotopes. Specifically, radioimmunoassay is used for testing of both clinical and experimental samples for viral, physiological and bacterial diseases, polypeptides and steroid hormones, drugs, pesticides and the like. The method of assay relies on the antibodies' specific ability to bind, *without preference*, a specific antigen (or hapten) whether the antigen be labeled or unlabeled. By combining a known amount of labeled antigen with an unknown amount of unlabeled antigen and by adding this mixture to a specific antibody, a certain percentage of the labeled and unlabeled antigen will be found to the antibodies. The percent of bound labeled antigen corresponds to the concentration of unknown, unlabeled antigen present in the mixture. The antibody-bound labeled and unlabeled antigens are separated from the unbound mixture and the radioactivity in one or both of these fractions is counted. To facilitate the radioactivity count, a liquid scintillator cocktail or solution is added to one or both of the separated fractions and placed in close proximity to a scintillator for a radioactive count. The radioactive energy released from the labeled antigens externally excites the scintillator causing bursts of light emissions which are then detected and measured. In instances where the radioactive material emits energy of suitable intensity, e.g., radioactive iodine, the phosphor may be eliminated or incorporated in the counting mechanism.

When the scintillator, the antibodies and the sample mixture of labeled and unlabeled antigens are carried by and combined in a solvent, the scintillator cannot be readily recovered for reuse nor can the antigen be readily separated from the antibodies, thus preventing the antigens to be reused for additional study and/or testing and must therefore be discarded.

Another problem is that when a solvent vehicle called the liquid scintillation "cocktail" is employed in a fully or partially automated radioimmunoassay system, the system requires a complicated, solvent resistant plumbing arrangement to pump and accurately introduce the solvent into the system. Another major problem is that the procedures of reacting the antigens and antibodies, separating the bound antigens from the unbound and measuring the radioactivity of these fractions are usually done as separate and sequential operations which are more time consuming than if they were combined into a single step operation. Even when all of these sequential operations are automated, the time required in moving the materials around and measuring radioactivity is undesirably more than if the automated system performed these operations in one place.

Objects of the Invention

It is therefore an object of this invention to provide a radioimmunoassay technique which permits the antigens, antibodies and the scintillators to be readily recovered for subsequent use and/or study. Another object is to provide a radioimmunoassay system which can be readily and economically automated. Another object is to provide a cell and method for performing radioimmunoassays in a single step and which will not require highly trained personnel to operate. Still another object is to provide a system of radioimmunoassay which is not only simplified but is also capable of enhanced and accurate reproducibility. Another object is to provide an immunoscintillation system that is adaptable to multiple testing on the same sample more simply, quickly and more economically than a liquid scintillation system. Still another more specific object is to provide a radioimmunoassay cell capable of performing at least three functions simultaneously: (1) to selectively bind or react specific labeled or unlabeled antigens with antibodies, (2) to separate the bound antigens from the unbound, and (3) to measure the radioactivity of the bound antigen, all in less time than it would take to do these functions separately. Still other objects and advantages will be readily apparent from the disclosure and description to follow.

Summary of the Invention

A means and method of radioimmunoassay has been developed whereby a mixture of labeled and unlabeled antigens are introduced into a cell containing solid, insolubilized or coated photon emitting substances and solid or insolubilized antibodies which selectively retain, with negligible or no preference, a portion of the labeled and unlabeled antigens. In one embodiment the photon emitting substances and the antibodies are chemically bound to an insoluble substrate. In another embodiment the phosphor and the antibodies are maintained separate by confining one from the other by means of a protective material. In either embodiment the radioactive energy released by the labeled antigen excites the photon emitting substance releasing bursts of fluorescent energy (photons) which are measured by a photon counting means. Studies have established that the counted or measured photons are proportional to the concentration of labeled antigens bound to the antibodies.

Since the antibodies can bind only a limited number of antigens and since the antibodies are incapable of discriminating or favoring either the labeled or unlabeled antigen (in some cases an isotope effect does exist but this has little effect on the system as long as it is constant), the concentration or number of labeled antigens bound to the antibodies is indirectly proportional to the concentration of unlabeled antigens present in the mixture. This provides a convenient method for quantitatively determining the concentration of a specific antigen in a sample. When the assay has been completed, the bound antigens are released from the antibodies by an eluting means permitting the same cell and materials to be used for additional testing. The released antigens may then be recovered and used in the performance of additional studies and/or testing.

A more complete understanding as to the application of this invention as well as a thorough review on the general principles involving radioimmunoassay can be found in Clinical Chemistry, Vol. 19, No. 2, 1973, pages 146–186.

DESCRIPTION OF THE PREFERRED EMBODIMENT

Figure 1:
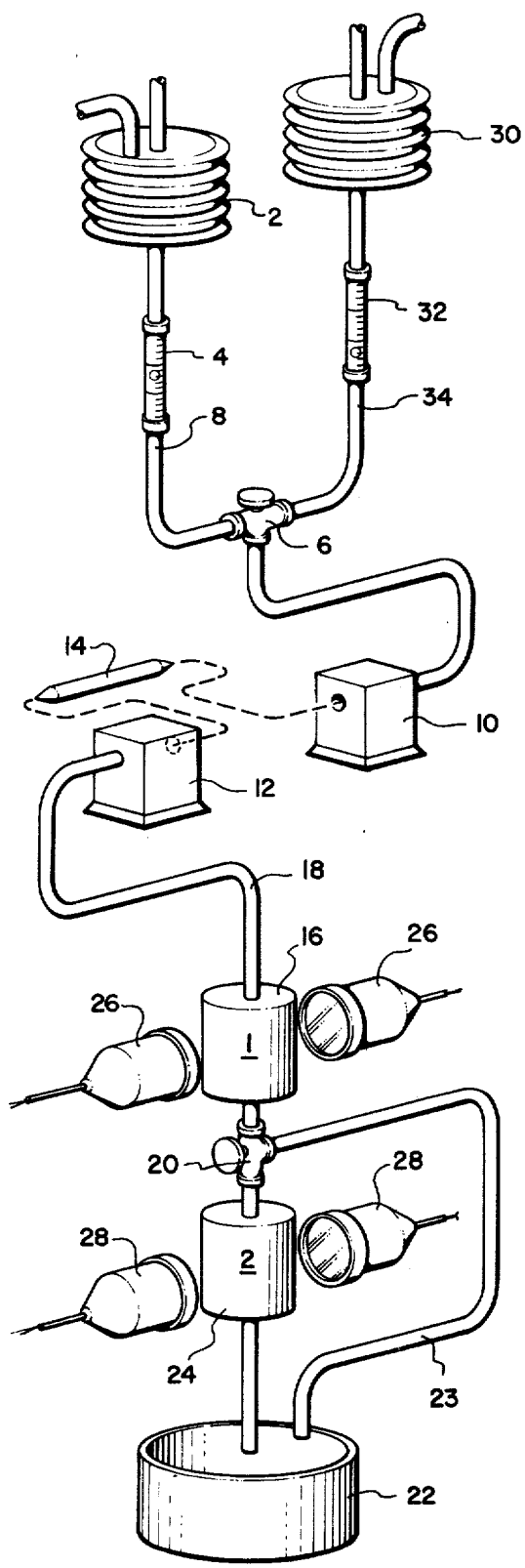
FIG. 1 is a pictorial flow diagram showing the major components making up the automated radioimmunoassay system of this invention.

Throughout the specification and claims of this invention certain words and terms will be used. For purposes of this invention, it is intended that these words and terms have the following meanings:

Antibodies

Antibodies are generally recognized as having a protein type base and were originally found in the gamma globulin fraction of blood as being the primary agent in producing an immune response. Their normal function in the blood is to recognize and chemically entrap or bind foreign substances that enter the main blood stream. In so doing, the antibodies render these foreign substances harmless. Antibodies may be conveniently produced by injecting a particular foreign substance into an animal's body and with periodic "booster" shots can force the production of relatively large quantities of an antibody specific for the foreign substance introduced into the blood stream. These foreign substances are generally referred to as antigens.

After a period of time, the animal injected with the foreign substances (antigens) is bled and the antibodies harvested. The antibodies are then purified and may be used for immunizing an individual against the foreign substance or may be used as a selective chemical binding agent in immunological tests as well as radioimmunoassays.

Although the specification and claims will make reference to antibodies and antigens generally, it is intended that this term also encompasses other binding materials capable of chemically binding a substance. For example, materials such as those described and listed below may be used in particular instances to bind a specific material:

A. Antibodies or antigens that have been coupled covalently to an insoluble matrix and still retain their immunological binding capacity (immunoadsorbents);

B. Antibodies or antigens that have been insolubilized by covalently coupling many antibody or antigen molecules together;

C. Naturally occurring proteins (other than antibodies) that have a high affinity for certain substances although they are generally not highly specific;

D. Naturally occurring materials, or products thereof, that bind specific compounds on a physiological relationship such as certain hormone receptor sites;

E. Enzymes, complement, RNA, DNA, cytochromes, chelating agents, charged or uncharged resins and plastics;

F. Antigens or haptens whereby certain antibodies or receptor substances are bound by using the antigen or receptor compound as the "binding" agent (technically the actual binding function is still done by the antibody or receptor substance; however, in this case the stationary material is now the antigen).

Antigens (Haptens)

Antigens are meant to encompass any foreign substance, whether organic or inorganic, which is capable of being bound to an antibody (binding material). For example, practically any organic or biochemical compound that is large enough to trigger antibody production or any smaller material which can be adsorbed or conjugated to the surface of a larger "carrrier" molecule and then used to trigger antibody production would be considered an antigen or hapten. "Conventional" antibodies are available commercially in blood fluids called antiserums (supernate from clotted and centrifuged whole blood) from such companies as Difco Laboratories, Cooke Laboratory Products, Miles Laboratories and others.

Scintillation counters

The scintillation counter consists of three essential parts: (1) a scintillating phosphor, (2) a photomultiplier tube, and (3) an optical reporting system.

A scintillating phosphor is a material capable of phosphorescence or luminescence (emission of photons) when excited by energy particles such as those generated by radioactive materials. Important inorganic phosphors are sulfides of zinc and cadmium activated with copper or silver, alkali halides, e.g., sodium iodide activated with thallium and tungstates of calcium and cadmium.

Organic phosphors are more frequently used and include napthalene and anthracene crystals, trans-stilbene, p-terphenyl, 2,5-diphenyloxazole, p-quaterphenyl and mixtures of the above.

Photomultipliers or photomultiplier tubes are readily available on the commercial market and comprise generally a photocathode tube capable of measuring the intensity of light emitted from a phosphor with preferably a low signal-to-noise ratio. The optical reporting system can be varied depending on ones particular need. Generally an electrical current is generated by the photocathode which is directly proportional to the intensity of light entering the tube. This electrical response is then measured and reported by gauges or print-out systems. Photon measuring and recording systems are available through Beckman Instruments, LKB Instruments and many others.

Protected antibodies and phosphors

In using the immunoscintillation cell of this invention for conducting assays, and particularly when the cell is used in an automated assaying system, a variety of solutions or solvents are generally introduced into the cell over a period of time. These solutions may include the sample itself, a vehicle for moving the sample through connecting tubing leading to the cell, a vehicle for introducing the sample into the immunoscintillation cell for assay, a rinsing solution for removing unbound materials from the cell and an eluting solution for removing the sample material bound within the cell after the assay has been completed.

These solutions or solvents may be aqueous or organic and may contain various inorganic salts, acids or bases as well as soaps, solubilizers, particulate matter and biochemicals. During the use of some of these substances, it is necessary that the activity of the binding and scintillator materials be retained and that the materials be able to be recovered after they are combined. To accomplish this, the immunoadsorbents and the scintillators must be "protected" from contaminating each other and must be "protected" from being solubilized in the carrier solvent.

This "protection" can be accomplished by chemically modifying the immunoadsorbent or scintillator, or by use of physical shields or separating barriers.

For example, when protected through their chemical makeup, the cell components would be largely unaffected by the solutions they were exposed to. When protected through use of physical shields, the immunoadsorbents and/or scintillators would be protected from the liquid carriers but would not be adversely affected in the performance of their intended function.

As indicated above, the protected antibodies and phosphors refer to antibodies and phosphors which are substantially unaffected by the liquid vehicle used for transporting an antigen or antibody whether this liquid vehicle be water or, when necessary, an organic solvent such as Xylene, ether and the like.

A protected phosphor would therefore include a phosphor which by its chemical makeup is not adversely affected by the liquid vehicle under conditions of use or a phosphor which is physically removed from the solvent by a plastic shield or by incapsulating the phosphor in a protective material. For example, a "plastic" phosphor can be used comprising 2% anthracene in transparent polystyrene, or a mixture of p-terphenyl and p,p'-diphenylstilbene in polyvinyltoluene (Pilot B, Pilot Chemicals Div., NEN.) The phosphor may also be sandwiched between two relatively thin transparent plastic, glass or resin sheets. The phosphors may also be chemically combined to a material, wherein the combination takes on "protective" properties.

Antibodies may likewise be protected by attaching or retaining the antibody to or within a material which would have the effect of insolubilization. For example, the antibody may be chemically linked to a support medium such as acrylamides or adsorbed to a polymeric surface which are insoluble in the liquid vehicle. In addition the antibody may be trapped within the pores of a porous material such as a molecular seive, charcoal and the like and retained within the pores even when exposed to a solvent material. Several schemes of "insolubilization" are depicted in FIGS. 2 – 5. In FIGS. 7 – 10 inclusive, the schemes shown in FIGS. 2 – 5 have been incorporated therein to show possible reaction chamber configurations.

Labeled antigens

Labeled antigens are foreign substances which have been altered to include a radioisotope. The physical characteristics and chemical properties of the labeled material is, for the most part, identical to the unlabeled material except that it is radioactive and is capable of disintegration during which energy in the form of alpha, beta or gamma rays is released. Materials are normally labeled by replacing one or several atoms in an organic molecule with an atom which is radioactive such as by substituting a hydrogen atom with $^3H$ (tritium) or a carbon atom with $^{14}C$ (radioactive carbon). In the alternative, the organic molecule may be altered by adding thereto a radioactive atom such as $^{125}I$. Various companies such as New England Nuclear now provide labeling services for essentially all types of organic compounds. Each of the above radioactive materials is capable of releasing energies in different forms and intensities. In each case certain modifications of the analyzing and detecting systems may be required in order to adapt the system for the radioactive material used. For example, the proximal relationship of the labeled material to the phosphor is more critical when tritium ($^3H$) is used and less critical when radioactive iodine is used. In the latter case the phosphor could be located outside the reaction cell and inside the counter and in some instances could even be eliminated provided that the energy levels are of sufficient intensity to measure radioactivity by other methods such as with a geiger counter.

Elutents

There are several ways by which the bound antigens and antibodies can be made to dissociate. In some cases rinsing with water solutions adjusted to various pH levels will accomplish removal of the antigen from the antibody. The use of several elution solvents can also achieve removal and are, therefore, effective elutents. (Reference: "Methods in Immunology and Immunochemistry" pp. 368–369, Table I. Academic Press, 1967 Ed., Curtis A. Williams.)

The most desirable eluting solutions are those that effectively cause antigens and antibodies to separate with minimal destruction of antibody or antigen activity. Buffered water solutions containing a solubilizing agent have been found to also have eluting powers. For instance, a 5% solution of a commercial solubilizer called Scintisol GP (Isolab Inc.) in water adjusted to pH 7.0 has eluting characteristics with minimal antibody inactivation.

Many types of solubilizers, soaps, detergents, emulsifiers, surfacants and wetting agents in water may also be used as eluting agents. Examples of such materials are: sulfated waxes, fats, oils, terpenes and higher alcohols; salts of alkylated aromatic sulfonic acids; ethanolamines alone or with fat acids (triethanolamine oleate);

rosin or salts thereof; synthetic emulsifiers such as mixtures prepared by partial esterification of glycerol with free fat acids or by glycerolysis of fats (glycerylmonostearate) or acetylation of monostearates; agents like carboxymethyl cellulose or "mechanical" emulsifiers like colloidal carbon or bentonite.

Other compounds that may be used as eluters are naturally occurring substances with emulsifying or surface active properties like: phospholipids (lechithins, cephalins), bile acids (cholic acid) and certain terpenes.

An aqueous eluting solution that contains one or more solubilizers as described above may also be capable of taking into solution or suspension other compounds that may or may not be normally soluble without the solubilizing agent. These additional compounds may be desirable for increasing the eluting potency of a particular solution.

Some compounds that may be added include saturated or unsaturated hydrocarbons (hexane, hexene), higher alcohols, mercaptans, ethers, aldehydes, ketones, acids, esters, fats and oils (ethyl mercaptan, propianaldehyde, acrolein, oleic acid, ethyl carbonate, glycerol tributyrate and the like). Other types of compounds that may still be added include amines and amides (butylamine), aromatic compounds in the above mentioned classes as well as silicon (silanes), halogen, nitrogen and sulfur derivatives of any of them. Mixtures and combinations of two or more of the above may also be used.

Application-Standard Curve

In applying the principles of radioimmunoassay for quantitatively measuring a particular antigen, a standard curve is first constructed by preparing several solutions or "standards" of known concentrations (titers) of the material (antigen) to be assayed. This is accomplished by weighing out known amounts of a purified antigen and dissolving same in an appropriate solvent to provide concentrations within the practical range of the assay.

A known or constant amount of an insolubilized antibody is then placed in each of several containers and one of the antigen solutions added. To each of the mixtures a known solution containing a labeled antigen is added. The amount of labeled antigen present in the solution will be one which is capable of providing a suitable response. The amounts of antibody, labeled antigen and the upper and lower concentration limits (titer) of unlabeled antigen to be used are determined emperically for determining operating parameters.

All of the final mixture-combinations will contain the same amount of antibodies, the same amount of labeled antigens but different and known amounts of the unlabeled antigen to be assayed.

The mixtures are agitated slightly to permit the antigens to be combined with the antibodies with the result that a proportional amount of the labeled and unlabeled antigens will be bound to the antibodies. Since the antibodies do not favor either the labeled or unlabeled antigen, the final ratio of labeled antigens bound to the antibody will depend on the relative concentration of unlabeled antigen present in the solution. In other words, the amount of labeled antigen bound to the antibodies will be inversely proportional to the amount of unlabeled antigen present in the solution. When the reaction in each of the containers has gone to completion, the insoluble antibodies containing the labeled and unlabeled antigens bound thereto are separated from the reacted antigens by precipitation or filtration. The bound, labeled antigens are then measured by the addition of the necessary amount of scintillator to the sample or, with high energy isotopes, by exposing the sample to an external scintillator and measuring the amount of luminescence produced.

The supernatant, or that material left unbound from the above reaction, may likewise be measured by the addition of a phosphor in the manner set forth above.

The count obtained represents the amount of labeled antigens bound to the antibody. The count also represents the amount of unlabeled antigens bound to the antibodies as determined by using a standard curve prepared as previously described. A graph is then prepared plotting percent bound counts vs. antigen concentrations.

After a standard curve has been constructed from known concentrations of the assayable material, it becomes possible to determine concentrations of the material in unknown samples. The procedure is to treat the unknown samples in the same manner the standard solutions were treated except that only the radioactive tracer and the antibody are added to the sample. When the samples containing the unknown amount of unlabeled antigen have amounts of tracer and antibody identical to those contained in the standard, the resulting percent bound determination will be indicative of the quantity of unlabeled antigen present in the sample.

For example, if the standard curve reports that 40% bound is equivalent to two milligrams of unlabeled antigen, an unknown sample which reports 40% bound would likewise contain two milligrams of unlabeled antigen.

Application-Assay

By utilizing the solid scintillating immunoadsorbent cell of this invention, a method and system of radioimmunoassay is now available which permits the antigens to be recovered for further testing and/or allows the antibodies to be reused for subsequent testing of samples. Such a system is shown in FIG. 1.

As shown in FIG. 1, a bellows type pump 2 is used to pump a controlled amount of a buffered rinse solution (Solution "R")through a flow meter 4 and three-way valve 6 via a tube 8. The tube is connected to a pair of sampling heads 10 and 12, bridged by a samplet tube 14, which in turn is connected to a solid scintillating immunoadsorbent cell 16 by a tube 18. The immunoadsorbent cell contains a protected phosphor and a protected antibody of the type depicted in FIGS. 2 through 5 inclusive. The cell itself may take on various shapes and designs 50, 52, 54 and 56 as shown in FIGS. 7 - 10 inclusive. The ideal cell is one having a highly exposed surface area to maximize luminescent emissions and binding activity.

The effluent from cell 16 passes on through a second three-way valve 20 which directs the effluent to either waste 22 via tube 23 or through a second immunoadsorbent cell 24 containing a protected phosphor and a second protected antibody. A pair of photomultipliers 26 and 28 are positioned in close proximity to both of the cells 16 and 24 respectively for measuring the photon intensity emitted by the phosphors. A second bellows pump 30 is also provided for pumping elutent (Solution E) through a flowmeter 32 and a three-way valve 6 via a tube 34.

In operation, a continuous flow of buffer solution is pumped through the lines leading to the immunoadsorbent cells. After the system has been stabilized, valve 6 is closed while the samplet connecting the sampling heads is replaced with a second samplet tube of specified volume containing a sample of antigens. Valve 6 is then opened to tube 8 and the buffer solution (Solution R) then carries the antigens (containing an unknown amount of unlabeled antigens and a known amount of identical but labeled antigens) through the immunoadsorbent cell (1). A portion of the labeled and unlabeled antigens are bound to the antibodies within the cell. The labeled antigens release radioactive energy which in turn excites the protected phosphors emitting photons which are measured by the photomultipliers. The amount of photons emitted are directly proportional to the amount of labeled antigens present in the sample. If desired, the remainder of the sample that went through cell 1 can be put through cell 2 immediately afterwards. Cell 2 would contain another antibody capable of performing an additional test for a different antigen on the same sample. If this test was not desired and/or cell 2 had been removed, then the solutions would be directed to the waste through valve 20 and tube 23.

After the reading has been completed, the three-way valve 6 is turned to close off the flow of Solution R and permits Solution E (an antigen eluting solution) to pass through the system stripping the antigens bound to the antibodies. The antibodies are now in condition to receive a second sample for testing.

Although the system schematically shown in FIG. 1 is manually controlled, it is evident that the system lends itself quite readily to full or partial automation.

Referring to FIGS. 2 through 5 inclusive, various techniques are shown for protecting the antibodies and phosphors.

Figure 2:
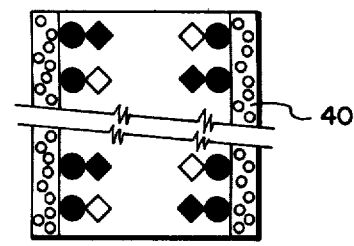
FIG. 2 diagrammatically shows a section of the solid scintillator cell shown in FIG. 1 wherein labeled and unlabeled antigens are bound to antibodies secured to a support medium which have phosphors imbedded therein.

In FIG. 2 the phosphors, depicted as circles, are imbedded within two opposing plastic sheets or within the sides of a tube 40. The internal surface of the sheets or plastic tube has attached thereto a number of antibodies depicted by darkened circles. As the antigens are carried between the sheets or through the tube, the labeled and unlabeled antigens, depicted by darkened and clear diamonds, are attached to the exposed antibodies.

Figure 3:
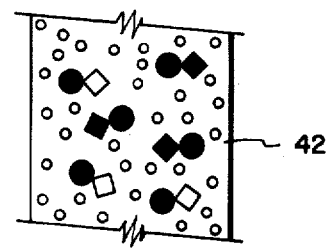
FIG. 3 shows a section of an embodiment wherein the cell comprises a plurality of spherically shaped solid phosphors and antibodies intermixed in a tubular member.

In FIG. 3 a tubular member 42 is filled with a mixture of insoluble crystalline phosphors, e.g., anthracene and insolubilized antibodies, e.g., antibodies adsorbed or chemically bound to plastic chips such as polystyrene.

Figure 4:
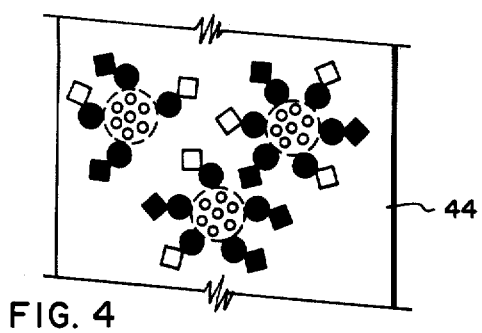
FIG. 4 is a sectional view of spherical plastic support members having phospors embedded therein and antibodies chemically attached to the surfaces thereof.

In FIG. 4 a tubular member 44 is filled with plastic balls having imbedded therein a phosphor and having attached to its surface an antibody.

Figure 5:
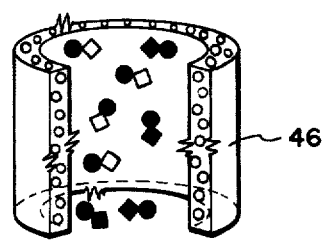
FIG. 5 is a double layered cut-away cylindrical container having phosphors sandwiched therebetween and wherein antibodies and antigens are attached thereto.
Figure 7:
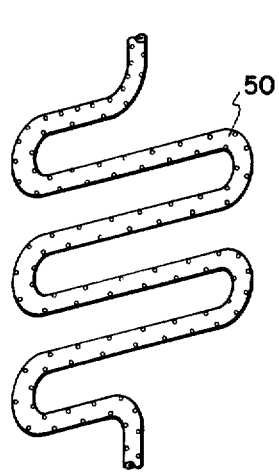
FIGS. 7 and 8 depict tubular solid scintillators wherein the antibody protein is attached to the inner wall of the round or flattened tubular members.
Figure 8:
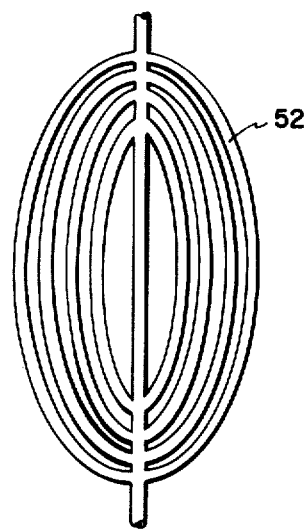
Figure 9:
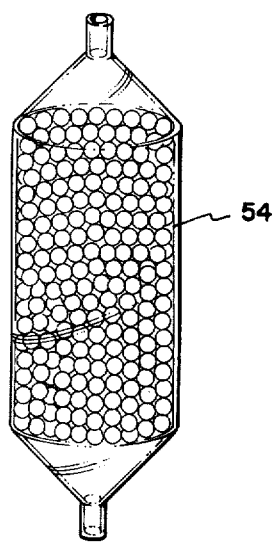
FIG. 9 depicts an arrangement wherein the solid scintillator is in the form of solid or porous beads with the antibody protein attached to the outer surface thereof.
Figures 10, 11:
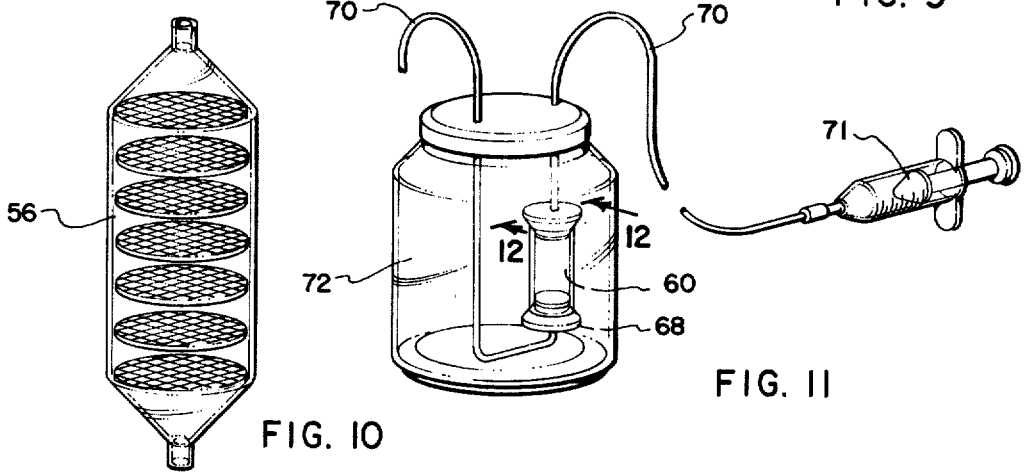
FIG. 10 depicts a system wherein the solid scintillator is in mesh form and the antibody protein is bound thereto.
FIG. 11 shows a specific test system used in demonstrating the immunoscintillation cell of this invention.

In FIG. 5 a tubular member 46 has imbedded therein a phospor similar to that depicted in FIG. 2. The tube is then filled with protected antibodies similar to those used in FIG. 3.

As is evident from the above, numerous combinations and variations of the above are possible. In each case, though, the critical feature is to provide a phosphor and antibody which is protected from the liquid buffer solution or other liquid vehicles passing through the immunoadsorbent cell.

A method for adsorbing an antibody to a polymeric surface is reported in Science, Vol. 158, pages 1570–1571 (1967) and Canadian Journal of Physiology and Pharmacology, Vol. 47, pages 803–813 (1969). According to the authors an antibody can be readily adsorbed to a polymeric surface by merely passing a solution of antibodies over a polymeric surface such as poly (tetrafluroethylene-g-isothiocyanatostyrene), sephadex-isothrocyanate, polypropylene, polystyrene and the like.

In addition to adsorption, an antibody may be chemically coupled to a polymer such as a cross-linked dextran (sephadex) and thereby insolubilized. The technique of insolubilization is essentially the same as that used for insolubilizing enzymes and other organic catalysts by chemically combining them to insoluble polymers like nylon, acrylic resins, cellulose and glass. A suitable procedure for insolubilization is reported in Nature, Vol. 210, pages 367–369 (Apr. 23, 1966). Nylon – FEBS Letters, Vol 10, No. 5, pages 325–377 (Oct. 1970). Cellulose — Immunochemistry, Pergamon Press 1965, Vol 2, pages 293–322. Glass — Analytical Chem. Vol. 45, No. 9, pages 1626–1632 (Aug. 1973). Polymerized antibodies — J. Biol. Chem., Vol. 242, pages 1651–1659, 1967.

EXAMPLE

Figure 12:
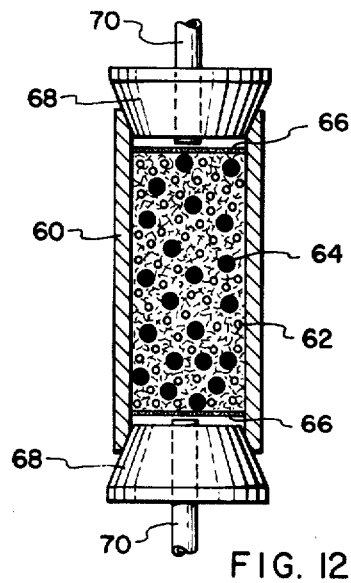
FIG. 12 shows an enlargement of the cell used in the test system shown in FIG. 11.

A solid scintillating immunoadsorbent cell (see FIGS. 11 and 12) was prepared by packing a glass vial 60 of 3.5 cm in length and having an ID of 0.5 cm with a mixture of 0.3 gm. of crystalline anthracene (scintillator) 62 and antitestosterone rabbit serum (antibody) covalently attached to a 3 mm. square of cotton filter pad 64 (Whatman type C No. 11204903). Prior to placement within the vial, the cotton pad was teased until it was fluffy. The antitestosterone antibody was covalently attached to the cotton pad by the CNBr method described on page 215 of "Radioimmunoassays Employing Immunoadsorbents, Acta Endocrinol," 63, suppl. 142,207 (1969). The antibody concentration was determined to have a titer of 1:150,000. With the anthracene and cotton antitestosterone intimately mixed within the vial, a piece of teflon matting 66 was placed in each end of the vial followed by a centrally bored rubber plug 68. A teflon tube 70 was then connected to each of the bored plugs to permit fluid ingress and egress into the packed cell. The various solutions were introduced into the scintillating immunoadsorbent cell by means of a syringe 71 connected to one end of the teflon tube. The cell was then placed into a standard 20 ml. glass scintillation vial 72 and lowered into the counting chamber of a Packard scintillation spectrometer (not shown).

A buffered rinsing solution (Solution R), a buffered eluting solution (Solution E) and testosterone standards (antigen) were then prepared. The prepared solutions had the following compositions:

Solution R comprised 0.004M $KH_2PO_4$, 0.016M $Na_2HPO_4$ and 0.05M NaCl in double distilled water and adjusted to a pH of 7.4.

Solution E comprised 0.02M $KH_2PO_4$, 0.08M $NaH_2PO_4$, 2% Scintisol G.P. (Isolab Inc., Akron, Ohio) and 2% purified clinical ether all of which were solubilized in double distilled water and adjusted to a pH of 7.37.

Testosterone Standards were prepared by dissolving 0.1 gm of crystalline Bovine Serum Albumin (BSA) from Pentex (Research Product Division, Miles Laboratories, Inc.) into 100 ml. of Solution R to give a 0.1% BSA buffered solution. A sufficient amount of 1,2$^3$H testosterone (New England Nuclear) was added to the 0.1% BSA solution to give a radioactive measurement of 187.5 nanocurries per ml. of solution. This was the equivalent of 0.6 nanograms per milliliter of buffered, $^3$H labeled testosterone solution, and is called the "zero" standard solution because it contains no unlabeled or "cold" testosterone.

The above buffered testosterone solution was then used to make a set of standards containing decreasing amounts of unlabeled or "cold" testosterone. A stock solution of unlabeled or cold testosterone was prepared by dissolving 10 mg. of dry testosterone powder obtained from Sigma Chemicals in 10 ml. of purified 100% ethyl alcohol. 0.02 ml. of the testosterone solution was then placed in a bottle and diluted to a 10 ml. volume by the addition of 100% ethyl alcohol. The final stock solution contained 2 micro grams of cold testosterone per milliliter of solution.

The first standard solution with cold testosterone was prepared by combining 0.32 ml. of the cold stock testosterone solution (2 micrograms/ml.) with 9.68 ml. of the 0.1% BSA buffered solution containing 0.6 nanograms/ml. of labeled testosterone. The final solution had a concentration of 64 nanograms/ml. of unlabeled testosterone and approximately 0.6 nanograms of labeled testosterone or a ratio of about 100:1 unlabeled to labeled testosterone.

A two-fold serial dilution was then performed to obtain five additional standardized solutions having 32, 16, 8, 4, and 2 nanograms per milliliter of unlabeled testosterone respectively and 0.6 nanograms per milliliter of labeled testosterone.

A seventh standard solution is the one originally prepared which contains 0.6 nanograms/ml. of labeled testosterone only.

In operation the 20 ml. Packard glass vial containing the immunoadsorbent-Scintillation Cell of this invention was placed into a counting well of a Packard scintillation spectrometer (Model 3320) with the inlet and waste teflon lines extending out therefrom. The well was covered and taped with a heavy black tape to prevent light leakage. The waste line was introduced into a waste container while the inlet line was adapted with several syringes for injecting various solutions into the cell.

With the Packard scintillation counter in "Repeat" position, 3 ml. of Solution E (Elutent) was introduced into the cell followed by 5 ml. of Solution R (Rinse) and a 5 minute count taken to measure background signals.

A series of assays were then made using 0.5 ml. of each of the standard testosterone solutions followed by 0.2 ml. of Solution R after which a one minute count was taken. After the one minute count was completed, a second 0.2 ml. sample of Solution R was introduced and a second one minute count taken. The above was repeated three more times until a total of 1. ml. of Solution R had been introduced and a series of five one minute counts taken. After the fifth count, four ml. of additional Solution R was introduced into the cell over a period of about 30 seconds and another 5 minute count taken. This last count represents the bound fraction; that is, the fraction of labeled antigens bound to the antibodies. After the bound count has been obtained, the bound antigens are then stripped from the antibodies by introducing 3 ml. of Solution E followed by 3 ml. of Solution R over a period of time of about 1 minute.

At this point another series of standard testosterone solutions were introduced into the cell following the steps above recited. The runs were made in duplicate and an average count reported in Table I below.

TABLE I

| Sample Identification | | |
|---|---|---|
| Sample | Labeled Testosterone nanograms/ml. | Unlabeled Testosterone nanograms/ml. | *Average % of bound labeled testosterone |
| 1. | 0.6 | 0 | 18.3 |
| 2. | 0.6 | 2.0 | 16.7 |
| 3. | 0.6 | 8.0 | 15.7 |
| 4. | 0.6 | 16.0 | 13.6 |
| 5. | 0.6 | 64.0 | 7.1 |

*The percent bound of labeled testosterones was calculated as follows:

$$\% \text{ bound} = \frac{\text{Bound Count - Background}}{\text{Total Count - Background}} \times 100$$

Figure 6:
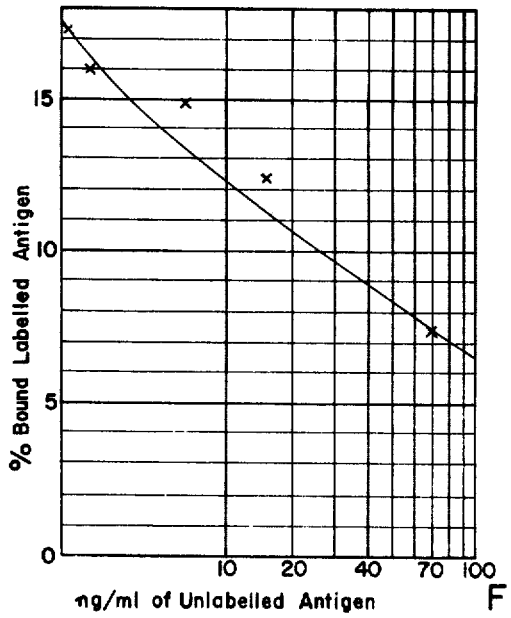
FIG. 6 is a chart showing the semilogarithmic relationship between percent bound labeled antigens vs. ng./ml. of unlabeled antigens present in the sample.

When the above results are plotted on semi-log graph paper, the resulting graph would be similar to the graph shown in FIG. 6.

The above runs indicate that a solid scintillating immunoadsorbent cell can be readily assembled for use in conducting a series of runs wherein the antigens originally bound to the antibodies are removed without adversely affecting the antibodies' binding capabilities. In addition the use of a solid or protected scintillator can also be effectively used in combination with the insolubilized or protected antibody for obtaining quantitative assays. In the past the samples used in the analysis became contaminated with the reactants used in the assay, making it impossible to reuse or retest the sample. With the system hereinabove described, the sample can be recovered for additional testing by application of an elutent while at the same time permitting the scintillator and antibody to be reused for additional assays.

Based on tests just completed, it appears to be possible to use the immunoadsorbent principle of this invention with other optical detection systems such as spectrophotometry, calorimetry, fluorometry, polarization spectrofluorometry and x-ray analysis. Using detection systems of the type recited above, no or very little radioactive materials or scintillation detectors would be needed.

While the invention has been described with reference to certain specific embodiments, it is understood that changes may be made by one skilled in the art and it would not thereby depart from the spirit and scope of the invention which is to be limited only by the claims appended hereto.

I claim:

1. An immunoscintillation composition comprising a protected photon emitting substance in proximal relation to an insolubilized immunoadsorbent capable of binding labeled and unlabeled bodies thereto.

2. The immunoscintillation composition of claim 1 wherein the photon emitting substance is a scintillator.

3. The immunoscintillation composition of claim 1 wherein the protected photon emitting substance is a scintillator protected by a polymeric material.

4. The immunoscintillation composition of claim 1 wherein the insolubilized immunoadsorbent is an antibody.

5. The immunoscintillation composition of claim 1 wherein the insolubilized immunoadsorbent is an antibody bound to an insoluble support medium.

6. The immunoscintillation composition of claim 1 wherein the protected photon emitting substance is a solid scintillator and the insolubilized immunoadsorbent is an antibody adsorbed to a polymeric substance.

7. The immunoscintillation composition of claim 1 wherein the immunoadsorbent is an antibody trapped within the pores of a porous material.

8. The immunoscintillation composition of claim 7 wherein the porous material is selected from a group consisting of molecular seives, charcoal and the like.

9. The immunoscintillation composition of claim 5 wherein the insoluble support medium is in the form of a tubular member.

10. The immunoscintillation composition of claim 5 wherein the insoluble support member is in the form of a sphere.

11. The immunoscintillation composition of claim 5 wherein the insoluble support member is in the form of a porous plate.

12. The immunoscintillation composition of claim 1 wherein the insolubilized immunoadsorbent is an antibody and the labeled and unlabeled bodies are antigens.

13. A method of radioimmunoassay comprising introducing a mixture of labeled and unlabeled bodies into an immmunoscintillation cell containing a protected photon emitting substance and an insolubilized immunoadsorbent capable of binding indiscriminately some of the labeled and unlabeled bodies and measuring the photons caused to be released by the labeled bodies.

14. The method of claim 13 including the step of introducing an eluting solution into said immunoscintillation cell for removing the labeled and unlabeled bodies from said immunoadsorbent after the photons have been measured.

15. The method of claim 14 wherein the elutent is a mixture of an organic solvent, water and a solubilizer.

* * * * *